United States Patent
Ma et al.

(10) Patent No.: US 9,907,531 B2
(45) Date of Patent: Mar. 6, 2018

(54) METHODS AND SYSTEMS FOR ULTRASONIC IMAGING

(75) Inventors: Zhongwei Ma, Shenzhen (CN); Linxin Yao, Renton, WA (US)

(73) Assignee: SHENZHEN MINDRAY BIO-MEDICAL ELECTRONICS CO., LTD, Shenzhen (CN)

( * ) Notice: Subject to any disclaimer, the term of this patent is extended or adjusted under 35 U.S.C. 154(b) by 513 days.

(21) Appl. No.: 13/028,857

(22) Filed: Feb. 16, 2011

(65) Prior Publication Data
US 2012/0152021 A1    Jun. 21, 2012

(30) Foreign Application Priority Data
Dec. 17, 2010  (CN) .......................... 2010 1 0594401

(51) Int. Cl.
| | | |
|---|---|---|
| *A61B 8/00* | (2006.01) | |
| *A61B 8/06* | (2006.01) | |
| *A61B 8/08* | (2006.01) | |

(52) U.S. Cl.
CPC ................ *A61B 8/06* (2013.01); *A61B 8/488* (2013.01); *A61B 8/5207* (2013.01); *A61B 8/5246* (2013.01); *A61B 8/0891* (2013.01)

(58) Field of Classification Search
CPC ....... A61B 8/06; A61B 8/5246; A61B 8/5207; A61B 8/488; A61B 8/0891; G01S 15/8979
USPC ........................................... 600/441; 73/632
See application file for complete search history.

(56) References Cited

U.S. PATENT DOCUMENTS

| | | | | |
|---|---|---|---|---|
| 5,720,291 A | * | 2/1998 | Schwartz ................ | A61B 8/06 128/916 |
| 5,846,200 A | * | 12/1998 | Schwartz ..................... | 600/443 |
| 6,139,501 A | | 10/2000 | Roundhill et al. | |
| 2008/0009737 A1 | * | 1/2008 | Takimoto et al. ............ | 600/454 |
| 2009/0012398 A1 | * | 1/2009 | Zhang et al. ................ | 600/453 |
| 2009/0192387 A1 | | 7/2009 | Yao | |

FOREIGN PATENT DOCUMENTS

| | | |
|---|---|---|
| CN | 101081170 A | 12/2007 |
| CN | 101081171 A | 12/2007 |
| CN | 101297217 A | 10/2008 |
| CN | 101347343 A | 1/2009 |
| CN | 101351724 A | 1/2009 |

(Continued)

*Primary Examiner* — Hien Nguyen
(74) *Attorney, Agent, or Firm* — Kory D. Christensen; Polsinelli LLP (57) ABSTRACT

A method for ultrasonic imaging comprises: emitting Doppler pulses to a target to be detected; performing a Doppler scan with Doppler pulses; receiving echo signals from the target, wherein the echo signals include Doppler pulse echo signals; processing the echo signals, wherein processing comprises an imaging step, the imaging step comprising parallel processing steps including a 2D image processing step, a flow image processing step, and a spectrum image processing step, wherein the 2D image processing step is configured for processing the echo signals to obtain 2D image signals, the flow image processing step is configured for processing the echo signals to obtain flow image signals, and the spectrum image processing step is configured for processing the echo signals to obtain spectrum image signals; and displaying the processed echo signals.

10 Claims, 7 Drawing Sheets

(56) References Cited

FOREIGN PATENT DOCUMENTS

| | | |
|---|---|---|
| CN | 101449984 A | 6/2009 |
| CN | 102370499 A | 3/2012 |
| WO | WO2007/069155 A1 | 6/2007 |

* cited by examiner

METHODS AND SYSTEMS FOR ULTRASONIC IMAGING

CROSS-REFERENCE TO RELATED APPLICATIONS

This application claims the benefit of Chinese Patent Application No. 201010594401.6, filed Dec. 17, 2010, which is incorporated herein by reference in its entirety.

TECHNICAL FIELD

The following disclosure relates to ultrasonic imaging.

SUMMARY OF THE INVENTION

Embodiments of methods and systems for ultrasonic imaging are disclosed. In one aspect, a method for ultrasonic imaging includes: emitting Doppler pulses to a target to be detected; performing a Doppler scan with Doppler pulses; receiving echo signals from the target, wherein the echo signals include Doppler pulse echo signals; processing the echo signals, wherein processing comprises an imaging step, the imaging step comprising parallel processing steps including a 2D image processing step, a flow image processing step, and a spectrum image processing step, wherein the 2D image processing step is configured for processing the echo signals to obtain 2D image signals, the flow image processing step is configured for processing the echo signals to obtain flow image signals, and the spectrum image processing step is configured for processing the echo signals to obtain spectrum image signals; and displaying the processed echo signals.

In another aspect, a method for ultrasonic imaging includes: emitting Doppler pulses and B pulses to a target to be detected, performing a Doppler scan with Doppler pulses and a B line scan with B pulses, and receiving echo signals from the target, wherein the echo signals including Doppler pulse echo signals and B pulse echo signals; processing the echo signals, wherein processing comprises an imaging step, the imaging step comprising parallel processing steps including a 2D image processing step, a flow image processing step and a spectrum image processing step, wherein the 2D image processing step configured for processing the echo signals to obtain 2D image signals, the flow image processing step configured for processing the echo signals to obtain flow image signals, and the spectrum image processing step configured for processing the echo signals to obtain spectrum image signals; and displaying the processed echo signals.

In yet another aspect, a system for ultrasonic imaging includes: a transmission and receiver module configured for emitting Doppler pulses to the target to be detected, performing a Doppler scan with Doppler pulses, and receiving echo signals from the target, wherein the echo signals include Doppler pulse echo signals; an echo signals processing module configured for processing the echo signals, wherein the echo signals processing module comprises an imaging module, the imaging module comprising parallel processing modules including a 2D image processing module, a flow image processing module, and a spectrum image processing module, wherein the 2D image processing module is configured for processing the echo signals to obtain 2D image signals, the flow image processing module is configured for processing the echo signals to obtain flow image signals, and the spectrum image processing module is configured for processing the echo signals to obtain spectrum image signals; and a display module configured for displaying the processed echo signals.

In still another aspect, a system for ultrasonic imaging includes: a transmission and receiver module configured for emitting Doppler pulses and B pulses to the target to be detected, performing a Doppler scan with Doppler pulses and B line scan with B pulses, and receiving echo signals from the target, wherein the echo signals include Doppler pulse echo signals and B pulse echo signals; an echo signals processing module configured for processing the echo signals, wherein the echo signals processing module comprising an imaging module, the imaging module comprising parallel processing modules including a 2D image processing module, a flow image processing module, and a spectrum image processing module, wherein the 2D image processing module is configured for processing the echo signals to obtain 2D image signals, the flow image processing module is configured for processing the echo signals to obtain flow image signals and the spectrum image processing module is configured for processing the echo signals to obtain spectrum image signals; and a display module configured for displaying the processed echo signals.

DETAILED DESCRIPTION

A medical ultrasonic system generally comprises a plurality of modules, such as a transducer (or probe), a transmission circuit, a receiver circuit, and a digital signal processing module. The transducer includes a plurality of array elements, each of which converts between electrical and ultrasonic signals. The transmission circuit activates the array elements to convert electrical signals into ultrasonic waves and emits the ultrasonic waves into the human body. The ultrasonic signals, scattered by the body tissue or blood flow, return to the transducer and are converted into analog electrical signals. The electrical signals are converted into digital signals in the receiver circuit. Thereafter, in the digital signal process module, useful signals are extracted from the digital signals, which are converted to visible images for evaluation by a physician.

As the tissues are different in various organs, the energy of the scattered echo signals received by the transducer is different. The transducer emits pulses and gathers a series of amplitudes of the scattered echo signals at different times based on the velocity of the ultrasonic wave. With a plurality of pulses emitted to different locations on a section, the transducer may receive a series of 2D data represented the difference of energy of the scattered signals corresponding to different positions at the section. The difference of energy may be mapped into different image gray scales so as to generate a black-and-white image (referred to herein as a 2D image) describing the structure of the body tissue. The pulse emitted by the transducer is usually called a B pulse.

During ultrasonic transmission, the Doppler Effect occurs due to the motion of the medium, such as blood flow. If the medium moves towards the transducer, the frequency of the scattered ultrasonic echoes increases; while if the medium moves away from the transducer, the frequency decreases. With the application of the Doppler Effect, a series of identical ultrasonic pulses are emitted by the transducer to a particular position in the body tissue, and the maximum detectable velocity of the medium is determined by the pulse repetition frequency (PRF). Since the blood flow keeps moving, the phase of echo may be changed. Autocorrelation estimation, a common analysis algorithm for phase difference, can estimate physical quantities with the phase difference brought about by the Doppler Effect, such as velocity, energy and variance. The velocity obtained by autocorrelation estimation may be mapped into pseudo-color information. The pseudo-color image is usually referred to as a color flow image (or simply "flow image"). The pulse emitted by the transducer is usually called a C pulse.

The flow image can be used to estimate the motion of flow at a cross section in the ultrasonic scanning. However, if it is desired to thoroughly estimate the tendency of a certain flow signal over time with accurate quantitative analyses, a pulse wave Doppler (PW) technique may be used. The corresponding image is usually called as Doppler frequency spectrum image (referred to herein as a "spectrum image"), and the pulse emitted by the transducer is usually called a D pulse. When detecting a target of interest, continuous pulses are emitted to the target by the transducer. The highest detectable flow velocity is determined by pulse repetition frequency (PRF). To observe higher flow velocity, the PRF needs to be raised; otherwise, to observe lower flow velocity, the PRF needs to be decreased.

There are several imaging modes in an ultrasonic imaging system, such as black-white imaging mode (to generate a 2D image), color flow imaging mode (to generate a flow image), and PW imaging mode (to generate a spectrum image). Different types of pulses are emitted under different imaging modes. That is, the B pulse is emitted under the black-white imaging mode, the C pulse emitted under the color flow imaging mode, and the D pulse emitted under the PW imaging mode. Under the black-white imaging mode, only B pulses are emitted in the system, and black-white imaging is carried out on gray scale data with regard to the amplitude of the scattered echo signals. Under the color flow imaging mode, B and C pulses are emitted in the system. When displaying a 2D image, the flow information, including velocity, variance, and energy in the region of interest, is displayed based on a color atlas. Under the PW imaging mode, the system emits B and D pulses to display the velocity information with the sampling gate by using a Doppler frequency spectrum, as well as displaying the 2D image.

Sometimes, a doctor needs to observe the 2D image, flow image, and spectrum image simultaneously, obtaining the status of blood flow of an interesting target and locating the region of interest by taking advantage of the dimensional image and the flow image. This is commonly referred to a "triplex imaging mode." Under the triplex imaging mode, different pulses, including B, C and D pulses, are needed to scan a position with time sharing. Due to the continuous movement of human organs and tissue, time sharing scanning at an identical position will cause unmatched images, and the scanning time for each type of pulse is limited. To obtain higher quality spectrum image, certain information about the 2D and flow images might be lost, and the frame rates of the 2D and flow images might be lower. However, to obtain higher quality 2D and flow images, a large amount of time may be needed to for scanning, and the scanning time for spectrum imaging is less. As a result, the quality of the spectrum image is reduced, and the continuity and time resolution are poor.

Figure 1:
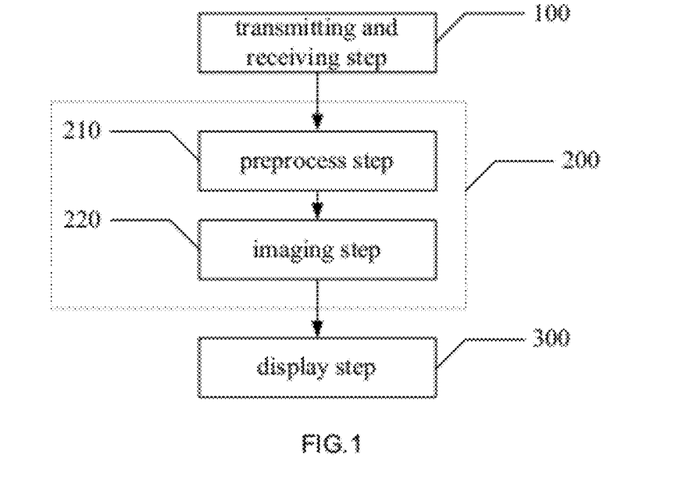
FIG. 1 is a flow diagram of a method for ultrasonic imaging.

Referring to FIG. 1, the method for ultrasonic imaging, according to one embodiment, includes a transmitting and receiving step 100 for emitting ultrasonic pulses to the target to be detected and receiving ultrasonic echo signals from the target; an echo signals process step 200 for processing ultrasonic echoes and output echo signals; a display step 300 for displaying the output from the echo signals process step. As described in greater detail below, the echo signals process step 200 may include a preprocessing step 210 and an imaging step 220.

In the transmitting and receiving step 100, a transmission logic unit may be used to generate transmission logic sequence based on requirements, wherein the logic sequence is transformed to transmission waveforms corresponding to array elements. The transmission waveforms are converted into ultrasonic signals via the transducer (or probe), after which the ultrasonic signals enter into human body tissue. The backscattered ultrasonic signals received by the transducer then are converted back into electrical signals.

In the preprocess step 210, analog time gain compensation (ATGC) technique may be used to compensate the attenuation of ultrasonic waves during transmission so that the energy of signals are unchanged with depth. After analog-to-digital conversion, the analog echo signals are converted to digital ultrasonic echo signals. Since each array element connects to its corresponding channel, signals from a plurality of channels enter into a beamformer to obtain radio frequency (RF) signals. Signals from different array elements can be converted to signals which are used to describe echo intensity from particular positions within body tissue. The digital echo signals, which have been beamformed, are processed using quadrature demodulation techniques. The ATGC, beamforming, and quadrature demodulation techniques mentioned herein are known by those skilled in the art, and are thus not described in detail here.

The imaging step 220 includes parallel processing of the ultrasonic echo signals after quadrature demodulation to generate the 2D, flow and spectrum images, i.e., the imaging step 220 comprises a 2D image process step, a flow image process step, and a spectrum image process step.

In the 2D image process step, an envelope detection algorithm may be used to generate echo intensity information so as to obtain 2D image. The envelope detection algorithm may take the absolute value of echo signals as a low-pass filter, or can be acquiring the signal modulus of echo signals. Any technique that can be used to generate information from echo signals may be used as known to those skilled in the art.

Because the Doppler signal produced by a stationary or a slowly moving tissue has a relative large amplitude and a relative low frequency, the presence of the signal in the tissue will have an unfavorable effect on the acquisition from weak blood flow. Thus, before the flow image process step and/or spectrum image process step, a wall filter may be used to filer low frequency echo signals from the tissue and blood vessel wall. Common wall filters include a finite impulse response (FIR) filter, an infinite impulse response (IIR) filter, and a polynomial regression filter. In one embodiment, the structure of the wall filter includes, but is not limited to, product of matrices, direct form, and transpose, and the wall filter includes, but not limited to IIR and FIR.

In the flow image process step, a process is used on the Doppler echo signals processed by the wall filter. In one embodiment, an autocorrelation estimation technique is used to calculate parameters describing blood flow signal, including the Doppler frequency shift, energy and variance. Thus the blood flow image signals are acquired. Any technique used to obtain parameters describing blood flow signal can be used as known to those skilled in the art.

In the spectrum image process step, the Doppler echo signals processed by the wall filter are calculated with frequency to obtain spectrum image signals. In one embodiment, the power spectrum of the Doppler echo signals is calculated by FFT to obtain spectrum image signals. Any technique for obtaining spectrum image signals can be used by those skilled in the art.

Figure 5:
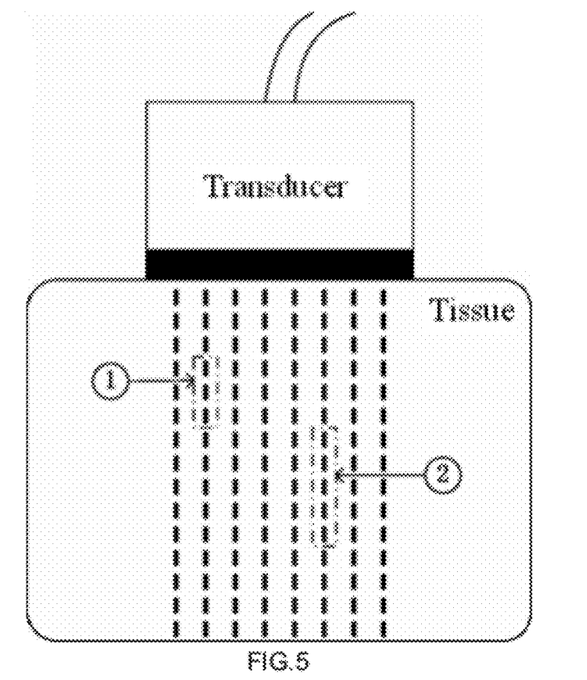
FIG. 5 is a schematic view of Doppler sampling.

According to requirements, if setting one or more sampling gates in the echo signals, spectrum image signals corresponding to the sampling gates can be obtained simultaneously. As shown in FIG. 5, ① and ② are two sampling gates set at two different positions on a plane in the tissue. The sizes of the sampling gates can be identical or not. Then data filtered by the wall filter respectively is accumulated to calculate the spectrum image. By setting sampling gates at a plurality of regions of interest (ROIs), the spectrum images corresponding to the ROIs can be calculated.

Figure 6:
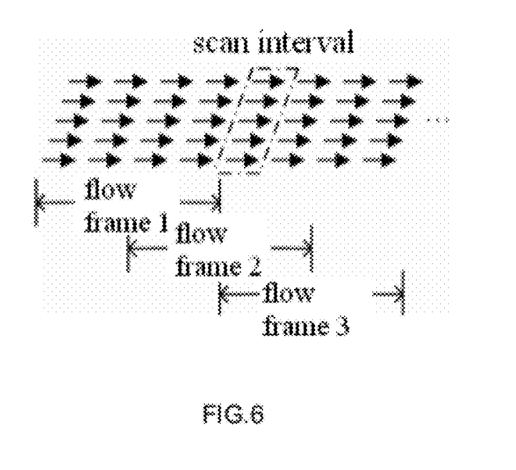
FIG. 6 is a schematic view of data overlap.

The three types of image signals (or any two of them, such as 2D and flow, 2D, and spectrum) can be outputted to the display at the same time. To ensure better frame rate and SNR, data reuse is needed sometimes. As shown in FIG. 6, a flow frame may be calculated in every four times of repeated transmission. If there is no data reuse between two calculations, the frame rate for display will be reduced by one time and less data will be used to reduce SNR. Therefore, in the display step 300, to increase the frame rate for display, a data overlap technique may be used to process the output from the echo signals process step. The overlapped image signals may be processed through a digital scan converter (DSC) to be ultrasonic image data, which can be displayed on a display. The data overlap technique is known to those skilled in the art and will not be described in detail here.

Figure 7:
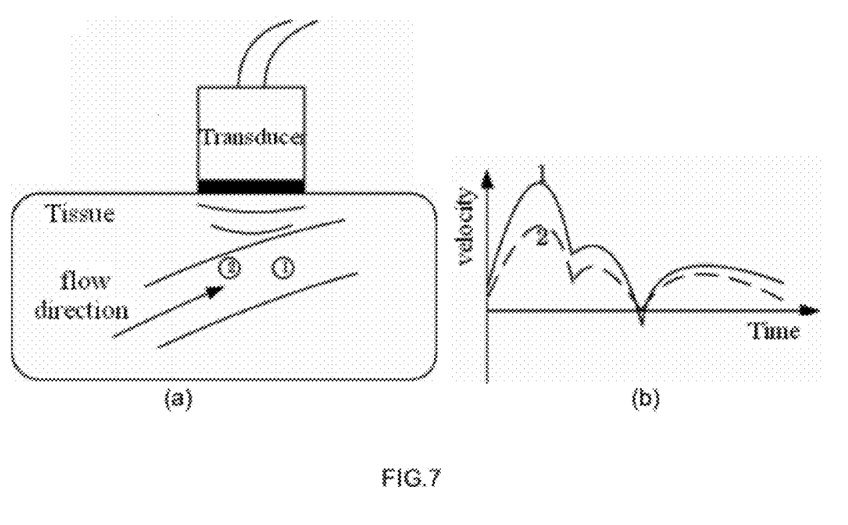
FIG. 7 is a schematic view of Doppler sampling and displaying.

When displaying a spectrum image, for example, when the system is scanning a blood vessel in the tissue, the velocities at different positions of the blood vessel are different. As shown in (a) in FIG. 7, two spectrum images can be obtained by setting two sampling gates ① and ② at the blood vessel, wherein the sizes of these sampling gates can be identical or not. The two spectrum images are synchronous and the time interval is less than 1/PRF; thus, the data at the sampling gates ① and ② which are filtered by the wall filter can be accumulated and displayed respectively, as shown in (b) in FIG. 7. If sampling gates are set at a plurality of ROIs, the spectrum images corresponding to the ROIs can be calculated and displayed.

It can be understood by those skilled in the art that if a series of pulses are continuously emitted by the transducer to different positions on a detective plane, enough echo data can be obtained to rebuild the image of the plane. If a series of pulses of pulse are continuously emitted by the transducer to a position, a tendency of echo signals over time can be obtained. If the tissue moves with respect to the transducer, the Doppler Effect will be observed. Using signal processing algorithms, the movement information can be detected to generate flow image or spectrum image.

Figure 2:
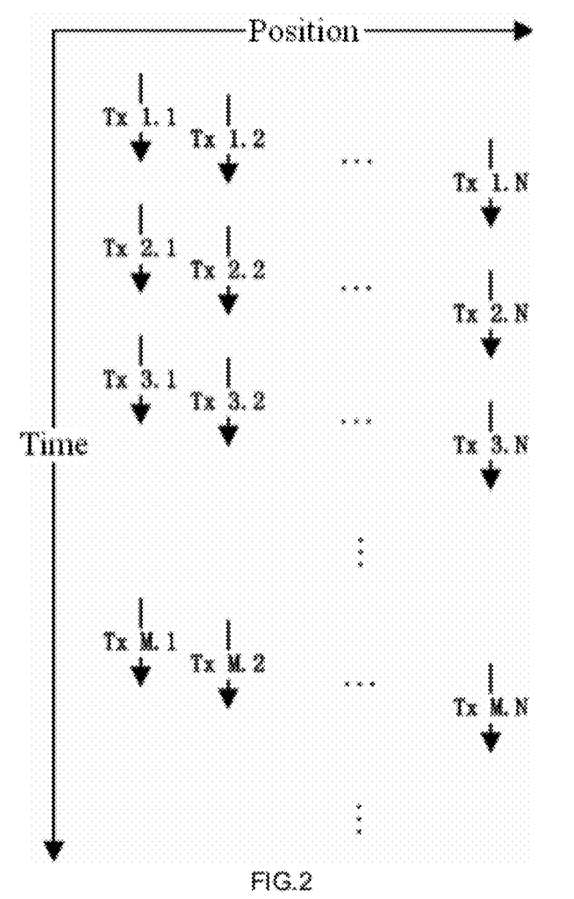
FIG. 2 is a schematic view of an emitted pulse sequence.

In one embodiment, the pulse emitted is only the Doppler pulse, which is used to generate the 2D, flow, and spectrum images simultaneously. The transducer emits the Doppler pulse to make Doppler scanning. The echo signals received by the transducer are regarded as Doppler pulse echo signals. As illustrated in FIG. 2, a complete Doppler pulse scanning frame includes Tx1.1 to Tx1.N, and a frequency spectrum package includes Tx1.1 to TxM.1. The frequency of Tx1.1 to Tx 2.1 is regarded as pulse repetition frequency (PRF), which determines the maximum detectable velocity and can be used to calculate the Doppler information of a scan line. The 2D image process step, flow image process step, and spectrum image process step are parallel processed in the imaging step 200. That is, the 2D image of the detected plane can be rebuilt by combining all of the scan lines (i.e., from 1 to N). The flow image can be obtained from the scan line of Tx1.1 to TxM.N after making velocity estimation on each scan line (such as Tx1.2 to TxM.2). If making distance accumulation on a scan line (such as Tx1.2 to TxM.2) at a certain deep range and calculating the information about Doppler, the spectrum image is calculated.

In another embodiment, the emitted pulses include Doppler pulses and B pulses. In the emitted sequence of pulses, the B pulse is emitted between two adjacent frames of a Doppler scan. Doppler pulses can be used to generate a 2D image, a flow image and a spectrum image; and B pulses can be used to generate the 2D image. The transducer emits the Doppler pulses to make Doppler scanning and emits B pulses to make B scanning. The echo signals received by the transducer include Doppler pulse echo signals and B pulse echo signals.

Figure 3:
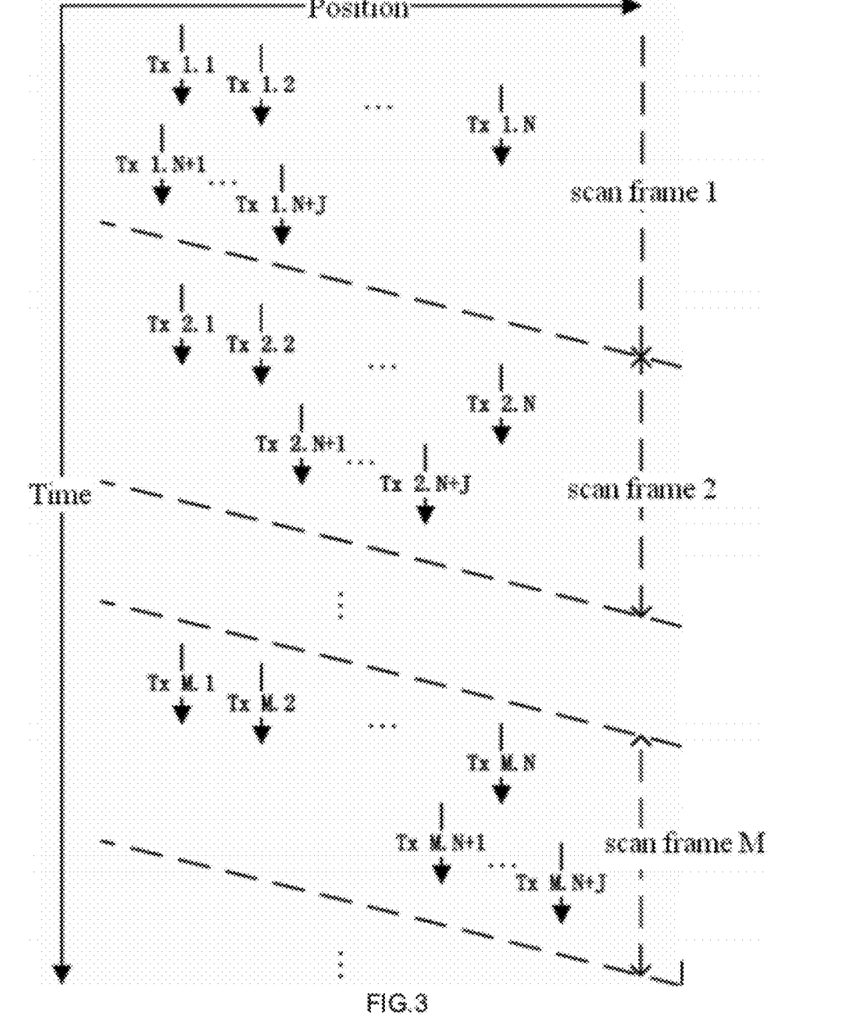
FIG. 3 is another schematic view of the emitted pulse sequence.

As shown in FIG. 3, the Doppler pulse scan is from Tx1.1 to TxM.N. J times of B scan is added in the scan interval between Tx1.N and Tx2.1, i.e., Tx1.N+1 to Tx1.N+J. The scan position can be identical or not to that in the first embodiment. The scan interval between Tx1.N and Tx2.1 is long enough for B scanning. Thus, J times of B scanning can be done every frame of Doppler pulse scan. Every n×J times of B scanning includes a complete 2D image, wherein n and J are arbitrary natural numbers.

The B pulse echo signals are processed to obtain the 2D image signals and the Doppler pulse echo signals to obtain 2D image signals, flow image signals and spectrum image signals. The 2D image signals can be enhanced by accumulating the 2D image signals obtained by the B pulse echo signals with the 2D image signals obtained by the Doppler pulse echo signals.

In another embodiment, although the emitted pulses in the embodiment are also Doppler pulse and B pulse, the emitted sequence is the B pulses are emitted between two adjacent Doppler scanning packages, wherein a Doppler scanning package comprises a plurality of frames of Doppler scan. Doppler pulses can be used to generate the 2D image, flow image and spectrum image; and B pulses can be used to generate 2D image. The transducer emits the Doppler pulses to make the Doppler scan and emits B pulses to make the B scan. The echo signals received by the transducer include Doppler pulse echo signals and B pulse echo signals.

Figure 4:
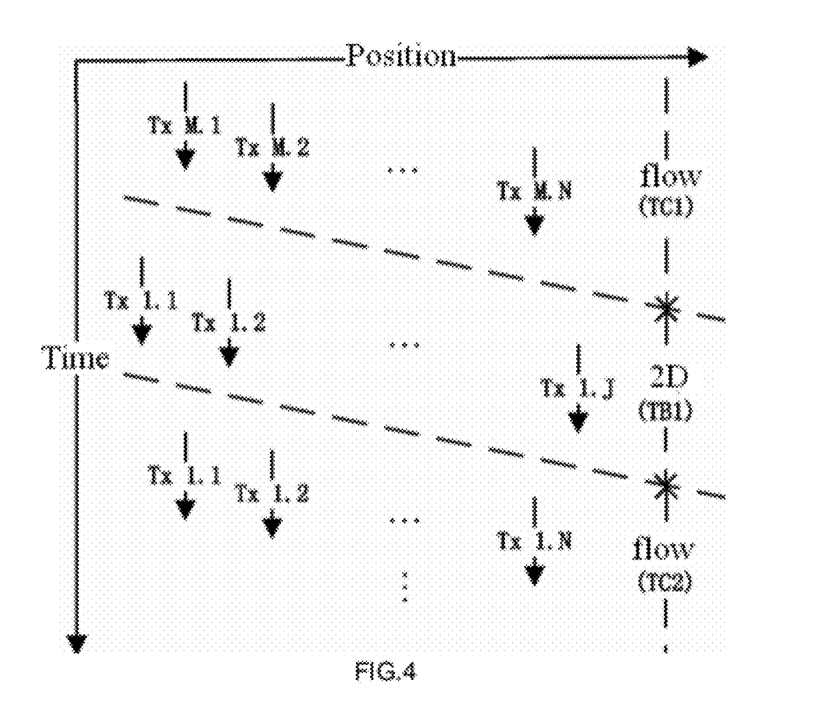
FIG. 4 is another schematic view of the emitted pulse.

As shown in FIG. 4, the difference between this embodiment and the previous embodiment is that the scan interval between two frames Tx1.N and Tx2.1 is not enough for a B scan. A B scanning may be inserted between two adjacent Doppler pulse scan packages, wherein each B scanning comprises J times of emission. The scan position can be identical or not to that of the Doppler scan. Every n frames of B scan consist of a complete 2D image (i.e., n×J times of emission), wherein n and J are arbitrary natural numbers; thus, the interval of two adjacent Doppler scan packages is enough for m frames of Doppler scan. That is, TxM.1 from package TC1 is extremely aligned to Tx1.1 from package TC2 in time, and the time interval is m/PRF.

In another embodiment, to obtain continuous flow data and improve the utilization rate of data, a gap filling algorithm based on the previous embodiment is used. The gap filling algorithm mentioned herein is known by those skilled in the art, and may include, but is not limited to, padding zero, linear interpolation, spline interpolation, and curve interpolation, and is thus not described in detail.

After determining the emitting pulse sequence by the aforesaid embodiments, if the Doppler scan keeps scanning continuously, the 2D image, flow image and spectrum image will be generated continuously. The subsequent steps, i.e., the imaging step can be that adopted shown in the FIG. 1, that is, the 2D image process step, the flow image process step, and the spectrum process step are parallel processed, and are not describe in detail here. In one embodiment, since the time on scan 2D image is short and will not evidently affect the quality of flow image and spectrum image, enough effective data can be used to the flow and spectrum scans to ensure the image quality under triplex imaging. Thus, the 2D image, flow image and spectrum image can be displayed at the same time with high frame rate and real-time. By setting one or more sampling gates in the echo signals, the spectrum image signals corresponding to the sampling gates can be obtained and displayed simultaneously.

Although various embodiments have been disclosed above, those skilled in the art will understand that various modifications, equivalent substitutions, and changes can be made. For example, in the imaging step, a single image signal can be generated based on requirements, or two image signals generated, or three image signals, etc. In the display step, the three image signals (or any two of them) can be output on the display synchronously.

Figure 8:
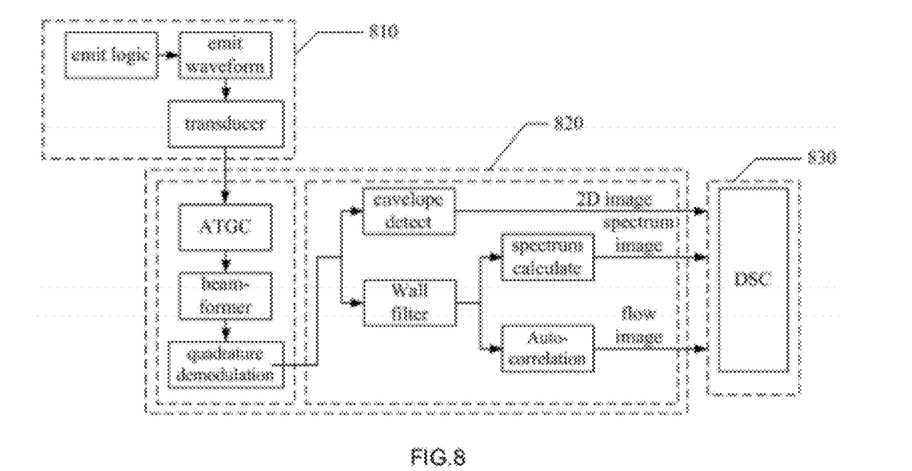
FIG. 8 is a block diagram of a system for ultrasonic imaging.

FIG. 8 is a block diagram a system for ultrasonic imaging according to one embodiment. As illustrated in FIG. 8, the system may include a transmission and receiver module 810 configured for emitting ultrasonic pulses to the target to be detected and receiving ultrasonic echo signals from the target; an echo signals process module 820 configured for processing ultrasonic echoes and output echo signals; a display module 830 configured for displaying the output from the echo signals process module. In one embodiment, the echo signals process module 820 may further include one or more parallel process modules, such as a 2D image process module, a flow image process module and a spectrum image process module.

According to another embodiment, the system includes a transmission and receiver module 810 configured for emitting ultrasonic pulses to the target to be detected and receiving ultrasonic echo signals from the target; an echo signals processing module 820 configured for processing ultrasonic echoes and output echo signals; a display module 830 configured for displaying the output from the echo signals process step. In one embodiment, the echo signals process module 820 comprises an imaging module which further includes parallel process modules, such as a 2D image process module, a flow image process module and a spectrum image process module. In one exemplary embodiment, the emitted sequence of pulses is created by emitting a B pulse between two frames of a Doppler scan. In another example, the emitted sequence is created by emitting B pulses between two adjacent Doppler scanning packages.

In the preceding description, numerous specific details were provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a non-transitory machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

What is claimed is:

1. A method for ultrasonic imaging by an ultrasonic imaging system that comprises a transducer, an echo signal processor and a display device, the method comprising:
   emitting, via the transducer, a sequence of ultrasonic pulses at a target to be detected, the sequence of ultrasonic pulses comprising Doppler pulses from which a Doppler image can be produced interleaved with B pulses from which a B-mode image can be produced;
   receiving, via the transducer, ultrasonic echoes from the target to obtain echo signals, wherein the echo signals are Doppler pulse echo signals and B pulse echo signals;
   processing the echo signals via the echo signal processor, wherein processing comprises:
       processing the B pulse echo signals to obtain B-mode image signals, obtaining additional B-mode image signals by processing said Doppler pulse echo signals, and combining the B-mode image signals obtained by the B pulse echo signals with the additional B-mode image signals obtained by the Doppler pulse echo signals to obtain new B-mode image signals;
       processing the Doppler pulse echo signals to obtain flow image signals, wherein the flow image signals are based on a velocity value for a specific position at first and second times,
       processing a portion of the Doppler pulse echo signals that are used to obtain the flow image signals to also obtain spectrum image signals based on a Doppler shift at or proximate to the specific position; and displaying a representation of the new B-mode image signals, flow image signals, and spectrum image signals on the display device.

2. The method of claim 1, wherein the B pulse is emitted between the two adjacent frames of a Doppler scan.

3. The method of claim 2, wherein displaying further comprises simultaneously displaying the B-mode image signals, the flow image signals, and the spectrum image signals.

4. The method of claim 3, wherein processing the Doppler pulse echo signals to obtain spectrum image signals comprises setting one or more regions of interest in the echo signals in order to obtain spectrum image signals corresponding to a regions of interest simultaneously.

5. The method of claim 3, wherein the displaying further comprises performing data overlap to the echo signals to increase a frame rate for display.

6. The method of claim 1, wherein, B scan comprises emitting at least one B pulse that is inserted between two adjacent Doppler scanning packages, each Doppler scanning package comprising a plurality of frames of Doppler scan without any B pulse.

7. The method of claim 6, wherein displaying further comprises simultaneously displaying the B-mode image signals, the flow image signals, and the spectrum image signals.

8. The method of claim 6, wherein processing the Doppler pulse echo signals to obtain spectrum image signals comprises setting one or more regions of interest in the echo signals in order to obtain spectrum image signals corresponding to a regions of interest simultaneously.

9. The method of claim 6, wherein processing the echo signals further comprises a filling step configured for performing gap filling to the echo signals before proceeding to an imaging step.

10. The method of claim 6, wherein the displaying further comprises performing data overlap to the echo signals to increase a frame rate for display.

* * * * *